United States Patent [19]

Haas

[11] 4,155,937

[45] May 22, 1979

[54] NOVEL POLYMERIZATION INITIATORS

[75] Inventor: Howard C. Haas, Arlington, Mass.

[73] Assignee: Polaroid Corporation, Cambridge, Mass.

[21] Appl. No.: 821,511

[22] Filed: May 2, 1969

Related U.S. Application Data

[63] Continuation-in-part of Ser. No. 630,222, Apr. 12, 1967, abandoned.

[51] Int. Cl.² ............................................. C07C 179/14
[52] U.S. Cl. ............................ 260/599; 260/453 AR; 260/453 PH; 260/544 K; 260/544 D; 260/544 N; 568/566; 526/208
[58] Field of Search ............................ 260/610 D, 599

[56] References Cited

FOREIGN PATENT DOCUMENTS 699768 12/1964 Canada .................................. 260/610 D

OTHER PUBLICATIONS

Haas et al., Chemical Abstracts, vol. 68 (1968), 40149r.
Haas et al., Journal of Polymer Science, "Aroyl Peroxides Containing Reactive Functional Groups," vol. 5, Part A-1, No. 11, Nov. 1967, pp. 2964-2966.
Greene et al., "J. Organic Chem.," vol. 28, pp. 2168-2171, (1963).

*Primary Examiner*—Bernard Helfin
*Attorney, Agent, or Firm*—Stanley H. Mervis

[57] ABSTRACT

Benzoyl peroxide compounds containing reactive substituents are used to initiate the formation of telechelic polymers.

4 Claims, No Drawings

NOVEL POLYMERIZATION INITIATORS

The instant application is a continuation-in-part of copending U.S. Application Ser. No. 630,222, filed Apr. 12, 1967, now abandoned in the name of Howard C. Haas.

The present invention is concerned with novel benzoyl peroxide compounds containing reactive moieties on the benzene rings, and polymers made therewith.

Although a great deal is known about free radical-producing initiators for polymerization of vinyl containing compounds very little is known about such initiators which contain reactive functional groups. Initiators of this type are useful in the preparation of polymer chains containing such groups at one or both ends of the chain. Such polymers may subsequently be reacted with other polymeric compounds to produce, for example, in the instance where said polymers terminate primarily by bimolecular coupling, block copolymers or cross-linked polymers having very long cross-links in the nature of block copolymers; or, for example, in the instance where said polymers terminate primarily by disproportionation, graft copolymers could be produced.

It is well known that the polymerization of vinyl-containing monomers takes place through three basic steps:

(a) Initiation, involving a decomposition of an initiator to yield a pair of free radicals and the subsequent addition of the free radicals to a monomer molecule.

R.+CH$_2$=CHX→RCH$_2$CHX., (b) Propagation, involving the successive addition of monomers to the radical formed,

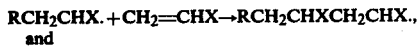

(c) Termination, which causes chain growth to cease. Termination may take place through any one of three mechanisms:

(1) bimolecular coupling of two growing chains;

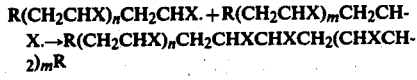

(2) disproportionation through transfer of a hydrogen atom from one growing chain to another;

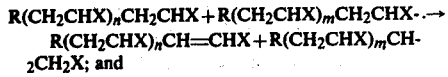

(3) chain transfer which involves the transfer of a hydrogen atom or other atom of the solvent or other molecule foreign to the growing chain and forms a new free radical;

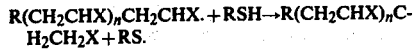

The instant invention is particularly concerned with the formation of polymers each chain of which is capped with a reactive group either on one or both ends, said reactive group having been contributed by the initiator utilized to begin the polymerization reaction. When such polymers are capped with reactive groups on both ends they are termed telechelic. An appropriate example of reactions which have been utilized to produce telechelic polymers may be found in a paper by Uraneck et al., *Journal of Polymer Science*, Vol. 46, 1960, wherein two methods for making such polymers are disclosed.

It is an object of the present invention to provide a method for synthesizing substituted benzoyl peroxide initiators containing functional moieties on the benzene rings.

It is a further object of the present invention to provide a novel method for making both telechelic polymers and polymers containing a reactive group only on one end of each chain.

Another object of the present invention is a novel method for making block copolymers and graft copolymers.

Other objects of the present invention will in part be obvious and will in part appear hereinafter.

The invention accordingly comprises the compound possessing the features and properties which are exemplified in the following detailed disclosure, and the scope of the application of which will be indicated in the claims.

For a fuller understanding of the nature and objects of the invention, reference should be had to the following detailed description.

The novel peroxides of the present invention may be represented by the formula:

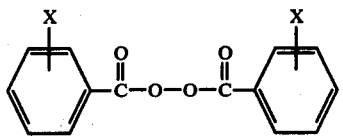

wherein X is a reactive group and particularly is selected from the group consisting of α-chloro monosubstituted alkyl groups, α-bromo monosubstituted alkyl groups, α-fluoro monosubstituted alkyl groups, each of said groups containing from 1 to 3 carbon atoms, inclusive; a formyl group; a formyl substituted alkyl group containing from 2 to 4 carbon atoms, inclusive; an isocyanate group; or an isocyanate substituted alkyl group containing from 2 to 4 carbon atoms, inclusive. It should additionally be understood that within the scope of the instant invention X is intended to encompass equivalents thereof.

Peroxide initiators containing functional groups, as disclosed herein, may be prepared, in general, by the reaction of hydrogen peroxide with a benzoyl halide, preferably, chloride compound containing the desired reactive groups, as illustrated below:

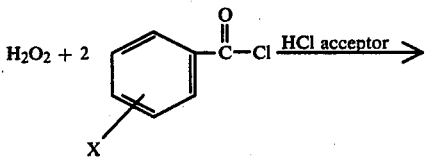

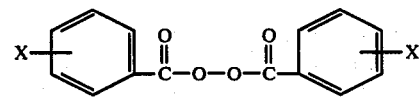

where X is as described in the paragraph next above. It is evident that the HCl involved would be reacted with the HCl acceptor, such as, for example, sodium hydroxide, sodium bicarbonate, etc.

Thus far, telechelic polymers have never been synthesized by the decomposition of a peroxide initiator which contains reactive functional groups. The advantages of such a system are obvious in that polymers of this type may be produced in one polymerization step without going through additional reactions to provide the desired end groups on the chains. It is evident that the method of termination which the polymers under consideration go through is of prime importance in determining whether the polymer will contain reactive groups on one or both ends of each chain. For example, if a polymer initiated by a peroxide compound containing functional moieties is terminated by disproportionation, the chains will contain functional groups only on one end. However, if the termination mechanism is bimolecular coupling, reactive groups will be found on both ends of the polymer chain.

Accordingly, it may be seen that if telechelic polymers are to be synthesized using the method of the present invention, only those monomers may be utilized which form polymers primarily by bimolecular coupling, as, for example, styrene, vinyl pyridine, vinyl naphthalene, etc.

The resultant telechelic polymers may be used in forming block copolymers by their sequential addition to polymers containing groups reactive with the functional groups on the telechelic polymers. For example, the benzyl alkyl halide or α halo ether-containing telechelic polymers would be reactive with polymers containing hydroxy groups, organo metallics as, for example, grignard type reagents, amine groups, anionic living polymers, mercapto groups, etc.; the telechelic polymers containing formyl groups would be reactive with polymers containing primary amines, 1,2-diols, 1,2-dimercaptans, 1,3-diols, 1,3-dimercaptans, organo metallics of the grignard reagent type, etc.; and the telechelic polymers containing isocyanate groups would be reactive with polymers containing hydroxyl groups, mercaptans, primary and secondary amines, carboxyl groups, organo metallics of the grignard reagent types, etc.

If polymers which are capped with reactive groups on only one end are to be synthesized, evidently, only those polymers may be utilized whose chains terminate primarily by disproportionation as, for example, methyl acrylate, methyl methacrylate, etc. Graft copolymers can then be formed by the same linkages described for the block copolymers, above.

The molecular weight of polymers made according to the present invention may be controlled somewhat by the relative amounts of initiator and monomer in the original system as well as by the medium and relative concentrations of constituents in the polymerization system employed as well as by the temperature of polymerization.

The following examples describe the preparation of benzoyl peroxide initiators containing reactive moieties and telechelic polymers made therewith. These examples are considered to be exemplary and should not be construed in a limiting sense.

EXAMPLE 1

Preparation of p-p'-bis-chloromethyl benzoyl peroxide 18 ml. of cold 15% sodium hydroxide and 7½ g. (0.04 m.) of p-chloromethyl benzoyl chloride (B.P. 141°/20 mm.) were added to 25 ml. of 10% hydrogen peroxide, stirred and maintained at 0° C. The additions were made dropwise always maintaining the mixture slightly alkaline. Stirring was continued for about three minutes and the product was filtered off and washed with ethanol. The product was recrystallized once from benzene and reprecipitated three times from chloroform into absolute ethanol. The product was found to contain 20.7% Cl which coincides with the theoretical chlorine content.

EXAMPLE 2

Preparation of chloromethyl telechelic polystyrene 2 g. of distilled styrene, and 4 ml. of dry benzene containing 60 mg. of p-p'-bis-chloromethyl benzoyl peroxide were sealed off under vacuum and heated at 70° C. for 20 hours. Polystyrene was isolated by precipitation into ethanol, purified by three additional reprecipitations into large quantities of ethanol, and dried under vacuum. The intrinsic viscosity, g. 100 ml$^{-1}$, in benzene at 25° C. was determined to be 0.183. A number average molecular weight of 9390 was obtained. Two terminal chloromethyl groups per chain should lead to a chlorine content of 0.755%. Analysis gave a value of 0.736% Cl, confirming again that termination in this system is predominantly by bimolecular coupling and that polystyrene containing reactive terminal benzyl chloride type groups can be produced. The presence of —C—Cl stretching is not detectable by infrared but absorption at 1720 cm$^{-1}$ shows that chain initiation is started by ClCH$_2$C$_6$H$_4$COO. radicals as well as ClCH$_2$C$_6$H$_4$. radicals.

EXAMPLE 3

Preparation of p-p'-bisformylbenzoyl peroxide

To 5.04 g. (0.03 m) of p-formylbenzoylchloride, (m.p., 41° C., B.P., 100° C./3 mm.) in 6 ml. of acetone, stirred and maintained between 0°–15° C., were added dropwise 1.71 g. (0.015 m.) of 30% hydrogen peroxide and excess sodium bicarbonate in 6 ml. of water. The reaction mixture was stirred for 10 minutes and the product filtered off. The peroxide was purified by dissolving in acetone and precipitation into water, drying under vacuum, and reprecipitation from benzene into hexane. The peroxide does not melt but explodes weakly on heating. Analysis for C and H gave: Found: C, 63.8; H, 3.40; Theoretical: C, 64.4; H, 3.35. The infrared spectrum is consistent with the structure of p-p'-bisformylbenzoyl peroxide.

EXAMPLE 4

Preparation of formyl telechelic polystyrene

Styrene monomer was polymerized using p-p'-bisformylbenzoyl peroxide and the polymer purified in the same manner as described above except that polymerization was carried out for 70 hours. A number average molecular weight of 8600 was obtained. The infrared spectrum of a film of this polystyrene (1.94×10$^{-2}$ mm. in thickness) shows clearly discernible carbonyl stretching absorptions for aldehyde at 1700 cm$^{-1}$ and ester at 1720 cm$^{-1}$. Using the corrected optical density of 0.13 for the 1700 cm$^{-1}$ band and a value of 300 for the extinction coefficient for carbonyl stretching, this sample is found to contain 0.224 moles of aldehyde per liter of polystyrene. Completely telechelic polystyrene of a member average molecular weight of 8600 (employing a density for polystyrene of 1.06) should be 0.246 molar in aldehyde so that here again a very large proportion of the polystyrene chains contain active aldehyde groups at both ends of the chain. If the corrected optical density of 0.11 for ester carbonyl (1720 cm$^{-1}$) is used to calculate the ester content (employing a value of 600 for the ester carbonyl extinction coefficient) a value of about 0.095 molar is obtained. This value implies that about 42% of the initiating species is the HOCC$_4$H$_6$COO. radical and the remaining 58%, the HOCC$_4$H$_6$. radical.

It will be appreciated from Examples 1 and 3 that the novel peroxides of the present invention may be synthesized by conventional techniques. As denoted above, such compounds may be directly made from the corresponding acid chloride by reaction with hydrogen peroxide and an HCl acceptor.

Exemplary techniques which may be employed in the synthesis of various acid chlorides which may be converted to the corresponding peroxides of the present invention are as follows:

(1) p-isocyanomethyl benzoyl chloride may be prepared by reducing p-cyanobenzoic acid and reacting the product with phosgene according to the following scheme:

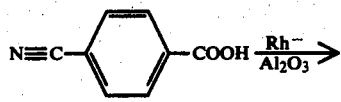

(2) p-isocyano benzoyl chloride may be prepared by reacting p-amino benzoic acid with phosgene which produces, under heating, the desired product according to the following scheme:

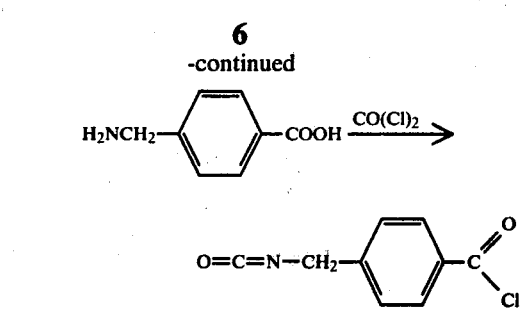

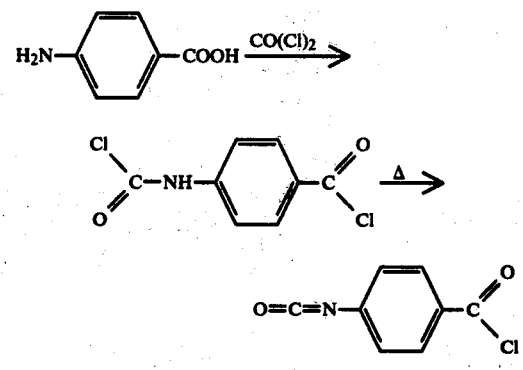

(3) p-formylmethyl benzoyl chloride may be prepared through a Grignard reaction, starting with p-bromo styrene, according to the following scheme:

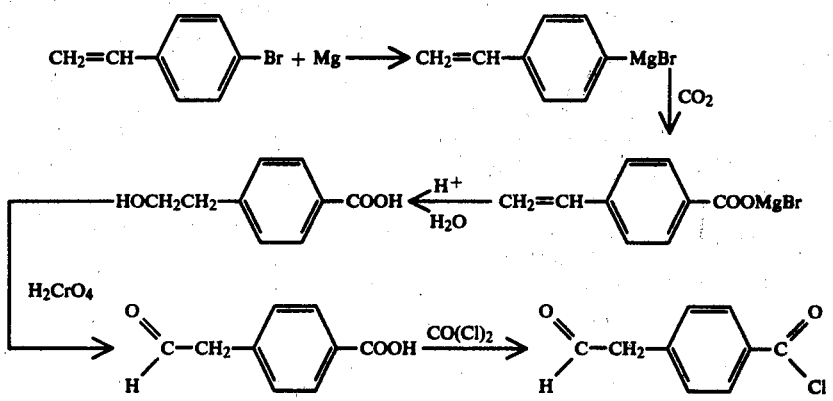

From the above examples, and synthesis schemes it may be seen that the instant invention affords the chemist a novel technique for utilizing certain peroxide initiators to provide novel polymers which may be used to form block copolymers, as cross-linking agents; to form graft copolymers, etc. Examples of suitable initiators within the scope of the present invention are:

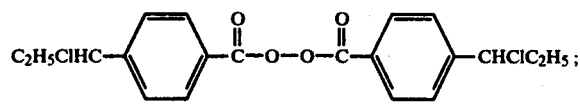

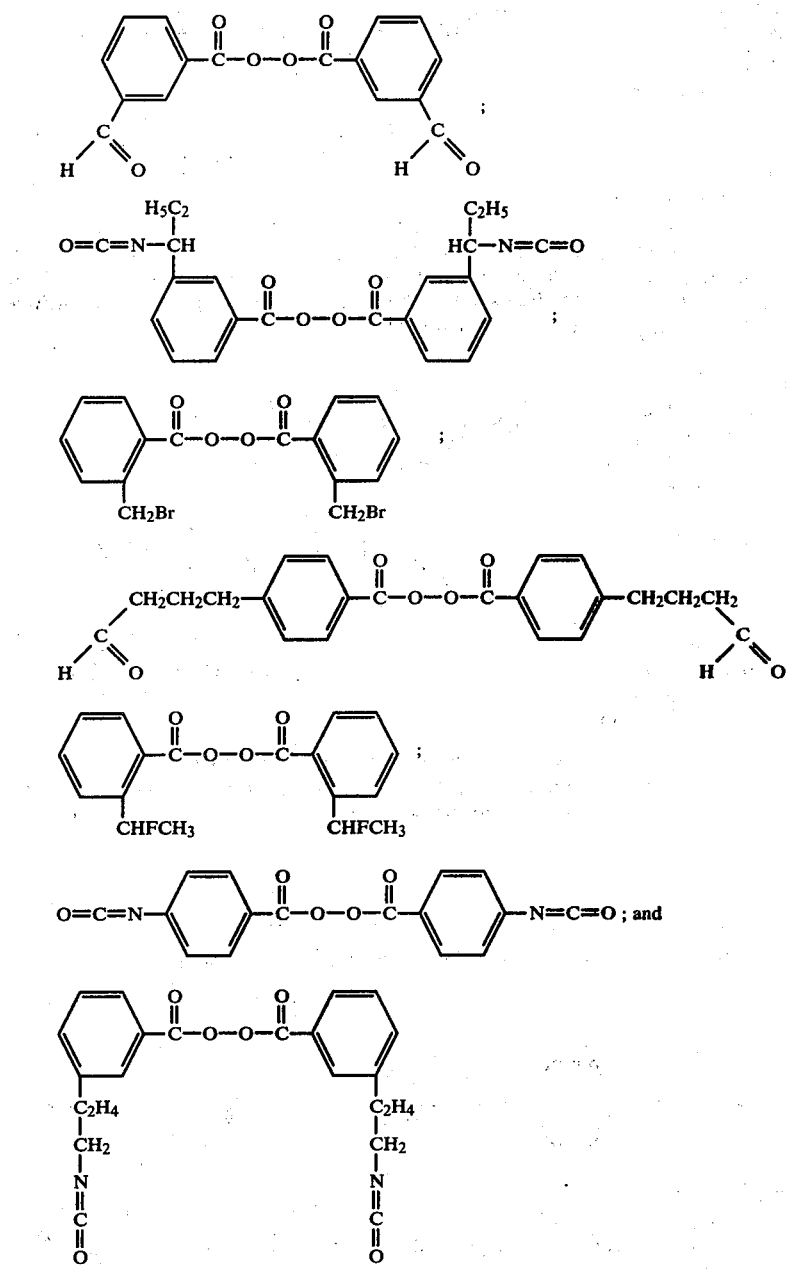
Examples of polymers formed by the method of the present invention utilizing an isocyanate-substituted benzoyl peroxide initiator, e.g.,
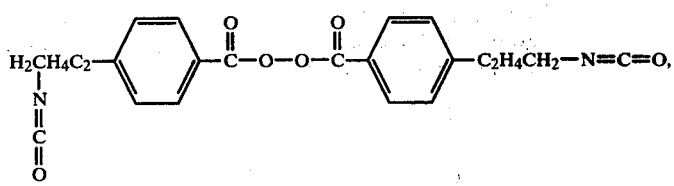
are;

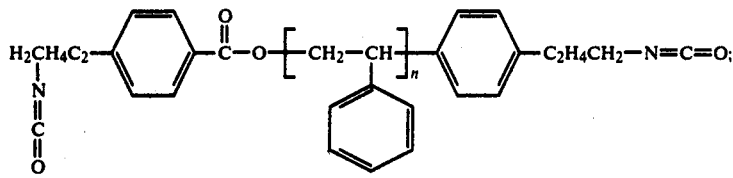

and

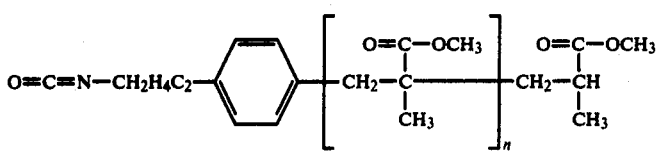

In the first instance, a bimolecular coupling terminating polymer is used, while in the second instance, a disproportionation terminating polymer is used. It is evident that the same types of polymer chains would be produced in the instances of initiation with benzoyl peroxides containing other functional groups within the scope of the instant invention.

Since certain changes may be made in the above process and products without departing from the scope of the invention herein involved, it is intended that all matter contained in the above description shall be interpreted as illustrative and not in a limiting sense.

What is claimed is:

1. A compound of the formula

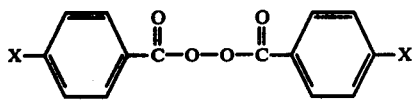

wherein X is selected from the group consisting of α-monosubstituted chloro, bromo and fluoro alkyl groups containing from 1–3 carbon atoms, inclusive; and

2. The invention of claim 1 wherein X is selected from the group consisting of α-monosubstituted chloro alkyl groups containing from 1–3 carbon atoms, inclusive; and

3. p-p′-bis-chloromethylbenzoyl peroxide.
4. p-p′-bis-formylbenzoyl peroxide.